United States Patent [19]
Puckett, Jr.

[11] 4,429,789
[45] Feb. 7, 1984

[54] SURGICAL SPONGE COUNTER

[75] Inventor: P. Brooks Puckett, Jr., Mequon, Wis.

[73] Assignee: Meridian Industries, Inc., Milwaukee, Wis.

[21] Appl. No.: 443,167

[22] Filed: Nov. 22, 1982

[51] Int. Cl.³ .............. A61B 19/00; B65D 5/44; B65D 27/08; A61F 13/00

[52] U.S. Cl. .................. 206/370; 206/438; 206/806; 206/527; 229/1.5 R; 229/15; 220/20; 220/18; 248/99

[58] Field of Search .............. 206/370, 438, 806, 526, 206/527; 220/18, 20; 229/1.5 R, 15, 69; 248/99

[56] References Cited

U.S. PATENT DOCUMENTS

| | | | |
|---|---|---|---|
| 457,390 | 8/1891 | Weeks | 229/15 |
| 2,399,056 | 4/1946 | Oller | 220/85 R |
| 2,715,493 | 8/1955 | Vogt | 206/527 |
| 2,770,513 | 11/1956 | Brown | 220/18 |
| 2,778,398 | 1/1957 | Edwards | 150/52 R |
| 3,391,698 | 7/1968 | Wiles | 220/20 |
| 3,397,804 | 8/1968 | Davis | 220/20 |
| 3,431,462 | 12/1969 | Chapel | 206/370 |
| 3,613,899 | 10/1971 | Schleicher et al. | 211/133 |
| 3,779,496 | 12/1973 | Welles | 248/99 |
| 3,948,390 | 4/1976 | Ferreri | 206/370 |
| 4,190,153 | 2/1980 | Olsen | 206/362 |
| 4,262,838 | 4/1981 | Mackenzie | 229/1.5 R |
| 4,312,447 | 1/1982 | McWilliams | 206/370 |

Primary Examiner—William T. Dixson, Jr.
Attorney, Agent, or Firm—Andrus, Sceales, Starke & Sawall

[57] ABSTRACT

A sponge counter includes a plurality of connected transparent flexible expandable open-topped plastic sponge-receiving bags which are mounted on a support which in turn can be hung from the edge of a kick bucket or the like. The bags are positioned close to the mouth of the kick bucket to provide high visibility of sponges placed therein. In the embodiment disclosed herein, the bags are interconnected in accordian-like fashion and the bag support is slotted to slip down over the kick bucket rim so that the counter assembly and bags extend radially out from the bucket wall. The slot is oriented so that the hanging counter assembly is positioned horizontally. The assembly is collapsible for easy disposal.

10 Claims, 4 Drawing Figures

SURGICAL SPONGE COUNTER

BACKGROUND AND SUMMARY OF THE INVENTION

This invention relates to a surgical sponge counter.

During surgical procedures, it is extremely important to account for all sponges that have been used in the operation. Previous known sponge counters, such as those disclosed in the above-identified patents, have utilized various types of compartments or sponge spacers, at least one of which is adapted to be used in association with the usual sponge receiving receptacle, normally called a kick bucket. These prior devices tend to be rather complex and relatively expensive to manufacture.

It is a task of the present invention to provide an improved sponge counter for use in association with a kick bucket or the like, which is simple in construction and low in cost, which provides high visability of the sponges, and which is easily disposable.

In accordance with the various broader aspects of the invention, the sponge counter includes a plurality of connected transparent flexible expandable open-topped plastic sponge-receiving bags which are mounted on a support which in turn can be hung from the edge of a kick bucket or the like. The bags are positioned close to the mouth of the kick bucket to provide high visibility of sponges placed therein.

In the embodiment disclosed herein, the bags are interconnected in accordian-like fashion and the bag support is slotted to slip down over the kick bucket rim so that the counter assembly and bags extend radially out from the bucket wall. The slot is oriented so that the hanging counter assembly is positioned horizontally. The assembly is collapsible for easy disposal.

BRIEF DESCRIPTION OF THE DRAWINGS

The accompanying drawings illustrate the best mode presently contemplated by the inventor for carrying out the invention.

In the drawings.

DESCRIPTION OF THE PREFERRED EMBODIMENT

Figure 1:
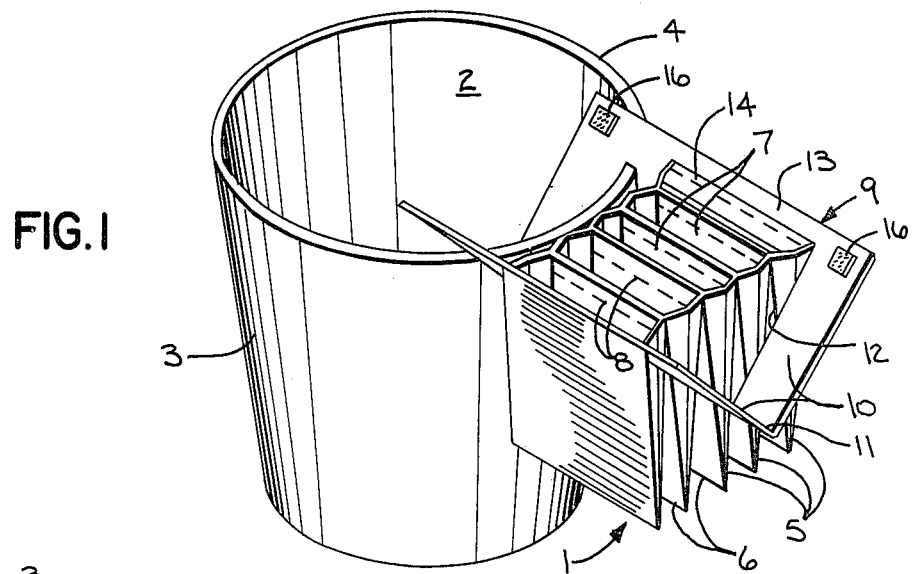
FIG. 1 is a perspective view of the surgical sponge counter of the invention attached to a kick bucket.

As shown in the drawings, the concepts of the invention are directed to a surgical sponge counter 1 which is adapted to be mounted, for example, on a sponge receiving receptacle such as a kick bucket 2 having a slanted annular wall 3 and top rim 4.

Counter 1 is adapted to receive a number of used sponges during an operation so that all sponges can be visually accounted for. For this purpose, counter 1 includes a plurality of closely adjacent interconnected bags 5 which are made of transparent flexible plastic material such as polyethylene film. Bags 5 are shown as being closed along their bottom edges 6 and expandable upwardly to open mouths 7 when in use. As shown, the adjacent mouth portions of adjacent bags 5 are secured together along a horizontal line of securement 8, as by an adhesive, heat sealing or the like. Line 8 is shorter than the full width of bags 5 to permit them to open in an accordian-like fashion.

The group of bags 5 is held in position in counter 1 by a support 9 which in this instance comprises a frame of paperboard or like material heavier than bags 5 and which comprises a pair of connected planular panels 10 which are hinged along one edge, as at 11, and free to be opened to a V-shape or closed as desired. Support 9 is provided with an enlarged opening 12 which forms a bag receiving means having facing upper edge portions 13. The two outermost bags of the group of bags 5 are secured in any suitable manner to edge portions 13 along a line of securement 14 which, like line 8, is shorter than the full width of the bags.

Figure 2:
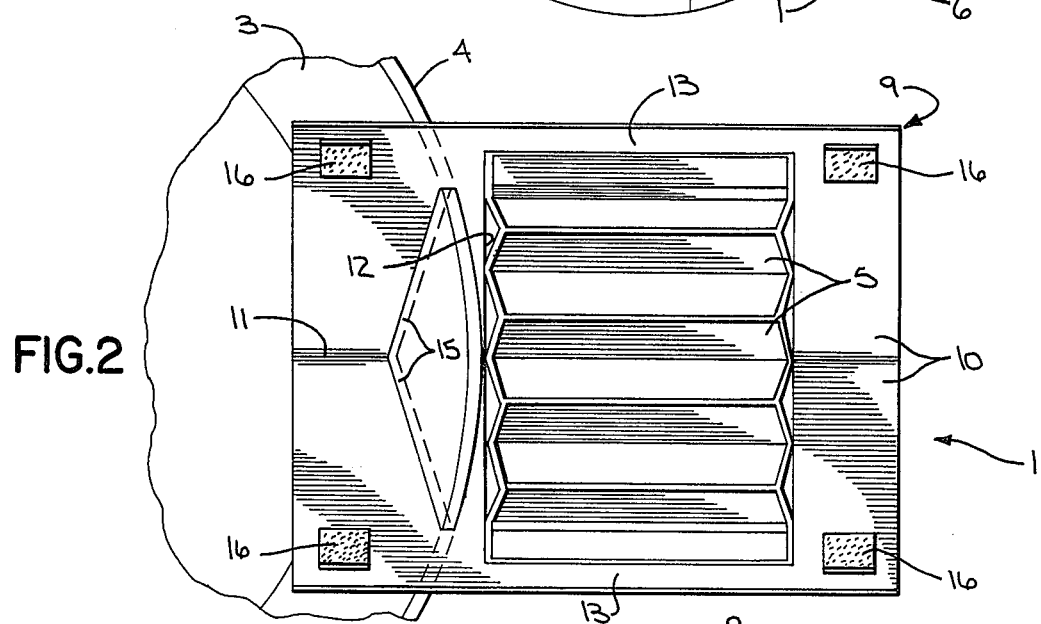
FIG. 2 is an enlarged top plan view of the sponge counter, as attached to the bucket.
Figures 3, 4:
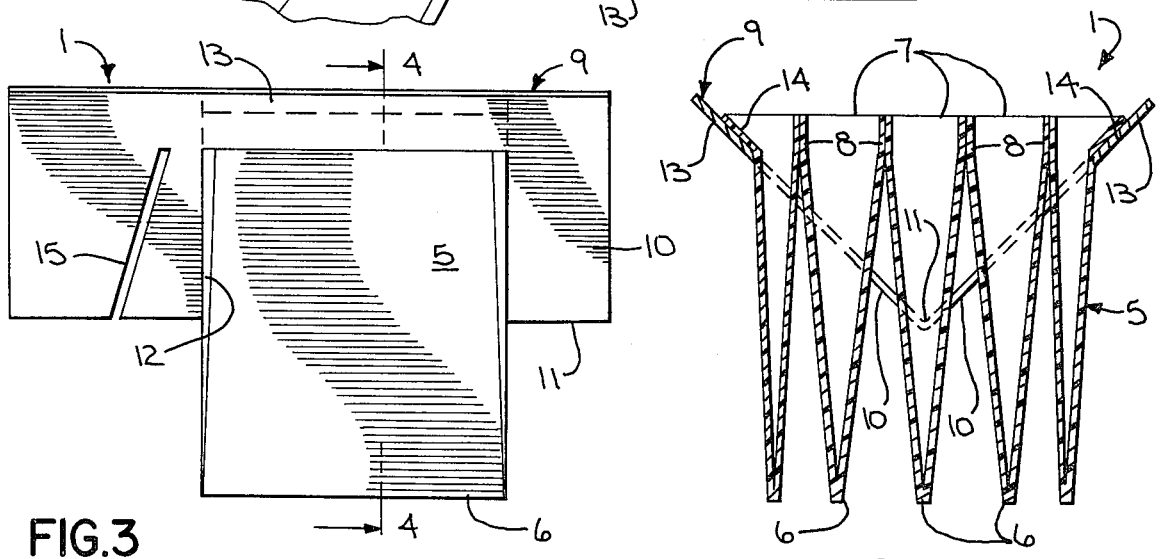
FIG. 3 is a side view of the sponge counter in closed position.
FIG. 4 is a central vertical section taken on line 4—4 of FIG. 3, when in open position.

Support 9 is adapted to be attached in open position to kick bucket 2, with bags 5 being open and hanging downwardly therefrom. For this purpose, a broken away portion such as a slot 15 is formed in panels 10 for fitting down over bucket rim 4 when panels 10 are open. In the open position, slot 15 is V-shaped relative to a transverse plane passing through support 9. See FIG. 2. In the folded closed position, or from the side, as shown in FIG. 3, slot 15 can be seen to extend at an angle from hinged edge 11, said angle corresponding to the angle the slanted bucket wall 3 assumes relative to the vertical. Thus, when counter 1 is expanded and mounted to kick bucket 2, the counter assembly will extend radially outwardly from the bucket and be disposed generally horizontally. Several counters may be mounted side-by-side on the same bucket.

During an operation, used sponges, not shown, are inserted into bags 5, where the sponges themselves and any blood or the like are highly visible. After the operation and when all sponges are accounted for, counter 1 may be lifted from bucket 2, panels 10 folded closed to collapse bags 5, and the panels secured together in any suitable manner. As shown, cooperating strips or tabs 16 of Velcro or other adhesive are disposed on facing surfaces of panels 10 to hold them in closed position. When panels 10 are closed, outer edge portions 13 sealingly hold bag mouths 7 in closed position to substantially prevent escape of material from the bags. Counter 1 may then be dumped into kick bucket 2 or otherwise disposed of. Various modes of carrying out the invention are contemplated as being within the scope of the following claims particularly pointing out and distinctly claiming the subject matter which is regarded as the invention.

I claim:

1. A surgical sponge counter for attachment to a kick bucket or the like during an operation, comprising:
    (a) a plurality of closely adjacent interconnected transparent expandable bags forming a group of bags,
    (b) said bags having closed bottom edges and having top mouths adapted to be openable upon expansion of said bags for receiving the sponges,
    (c) means for supporting said bags in generally vertical hanging position,
    (d) means securing at least some of said bags to said bag supporting means,
    (e) and means on said bag supporting means for attaching the latter to a kick bucket.

2. The surgical sponge counter of claim 1 wherein:
    (a) said bag supporting means comprises a panel of material heavier than said bags, (b) and said panel is provided with a broken away portion for fitting down onto a kick bucket rim.

3. The surgical sponge counter of claim 2 wherein:
(a) said bag securing means is disposed adjacent the top of said bags,
(b) and said panel is foldable onto itself.

4. The surgical sponge counter of claim 3 which includes means for holding said foldable panel in folded position.

5. The surgical sponge counter of claim 1 wherein:
(a) said bag supporting means comprises:
  (1) panel means of a material heavier than said bags and with said panel means being openable to a generally V-shape and closable along a hinged edge,
  (2) said panel means having a bag receiving opening forming facing upper edge portions to which the end bags in said group of bags are attached by said bag securing means,
(b) and said attaching means comprises a broken away portion forming a generally V-shaped slot in said panel means when the latter is open for fitting down onto a kick bucket rim.

6. The surgical sponge counter of claim 5 which is adapted for attachment to a kick bucket having a wall slanted at an angle to the vertical, and wherein said slot, in side elevation, is disposed at an angle to said hinged edge which corresponds to the said angle of the kick bucket wall so that, upon application of said counter to the kick bucket, said counter will extend horizontally outwardly from the bucket.

7. The surgical sponge counter of claim 5 in which, upon hingedly collapsing said panel means, said upper edge portions compress the tops of said bags to hold said bag mouths in closed position.

8. The surgical sponge counter of claim 7 wherein there is included means for holding said panel means in collapsed position.

9. The surgical sponge counter of claim 5 wherein the adjacent mouth portions of adjacent bags are secured together along a line which is shorter than the full width of said bags so that the tops of said bags open and close accordian-like when said panel means is moved between open and collapsed position.

10. The surgical sponge counter of claim 1 wherein:
(a) said bag supporting means comprises:
  (1) panel means of a material heavier than said bags and with said panel means being openable to a generally V-shape and closable along a hinged edge, (2) said panel means having a bag receiving opening forming facing upper edge portions to which the end bags in said group of bags are attached by said bag securing means,
(b) and said attaching means comprises a broken away portion forming a generally V-shaped slot in said panel means when the latter is open for fitting down onto a kick bucket rim,
(c) said counter being adapted for attachment to a kick bucket having a wall slanted at an angle to the vertical, and wherein said slot, in side elevation, is disposed at an angle to said hinged edge which corresponds to the said angle of the kick bucket wall so that, upon application of said counter to the kick bucket, said counter will extend horizontally outwardly from the bucket,
(d) the adjacent mouth portions of adjacent bags are secured together along a line which is shorter than the full width of said bags so that the tops of said bags open and close accordian-like when said panel means is moved between open and collapsed position,
(e) upon hingedly collapsing said panel means, said upper edge portions compress the tops of said bags to hold said bag mouths in closed position,
(f) and there is included means for holding said panel means in collapsed position.

* * * * *